(12) United States Patent
Bievenue et al.

(10) Patent No.: US 6,935,778 B2
(45) Date of Patent: Aug. 30, 2005

(54) METHODS AND DEVICES FOR ALIGNING AND DETERMINING THE FOCUSING CHARACTERISTICS OF X-RAY OPTICS

(75) Inventors: Thomas J. Bievenue, Delmar, NY (US); John H. Burdett, Jr., Charlton, NY (US)

(73) Assignee: X-Ray Optical Systems Incorporated, Albany, NY (US)

( * ) Notice: Subject to any disclaimer, the term of this patent is extended or adjusted under 35 U.S.C. 154(b) by 0 days.

(21) Appl. No.: 10/764,257

(22) Filed: Jan. 23, 2004

(65) Prior Publication Data

US 2004/0151281 A1 Aug. 5, 2004

Related U.S. Application Data

(63) Continuation-in-part of application No. PCT/US02/23754, filed on Jul. 26, 2002.
(60) Provisional application No. 60/308,311, filed on Jul. 27, 2001.

(51) Int. Cl.[7] .............................................. A61B 6/08
(52) U.S. Cl. ....................... 378/205; 378/206; 378/207
(58) Field of Search .............................. 378/43, 44, 84, 378/204, 205, 206, 207, 210; 250/505.1

(56) References Cited

U.S. PATENT DOCUMENTS 6,504,901 B1 * 1/2003 Loxley et al. ................ 378/84

* cited by examiner

Primary Examiner—David V. Bruce
Assistant Examiner—Courtney Thomas
(74) Attorney, Agent, or Firm—Kevin P. Radigan, Esq.; Heslin Rothenberg Farley & Mesiti P.C.

(57) ABSTRACT

Methods and devices for aligning an x-ray optic with a source of x-rays and methods and devices for determining a focusing characteristic of an x-ray optic are provided. The methods and devices simplify the process of aligning an x-ray optic device (for example, a polycapillary x-ray optic) to an x-ray source or for measuring a focusing characteristic, for example, the focal length or beam shape, of an x-ray optic. In one aspect, the device includes a housing having a first aperture adapted for receiving an x-ray optic and a surface having an x-ray flourescent material from which visual fluorescence occurs when impinged by x-rays. The size and shape of fluorescence from the surface may be varied by moving the surface to determine, for example, the focal length of the x-ray optic.

45 Claims, 2 Drawing Sheets

METHODS AND DEVICES FOR ALIGNING AND DETERMINING THE FOCUSING CHARACTERISTICS OF X-RAY OPTICS

CROSS-REFERENCE TO RELATED APPLICATION

This application is a continuation of PCT application PCT/US02/23754 filed Jul. 26, 2002, and published under PCT Article 21(2) in English as WO 03/012797 A1 on Feb. 12, 2003. PCT/US02/23754 claimed the priority of U.S. provisional application 60/308,311, filed Jul. 27, 2001. The entire disclosures of both are incorporated herein by reference.

TECHNICAL FIELD

This invention relates generally to apparatus and methods used for focusing or aligning x-ray optics. Specifically, the present invention provides improved methods and apparatus for aligning x-ray optics with x-ray sources to provide increased x-ray intensity on an x-ray target.

BACKGROUND OF THE INVENTION

X-rays are commonly used in many commercial and medical applications. For example, in medical applications x-rays are used to treat tumors or other ailments. In the semiconductor industry, x-rays are used for surface analysis to detect surface contamination on semiconductors. Typically, to achieve effective treatment or surface analysis, x-rays are directed to the area of interest by x-ray diffracting devices referred to in the art as x-ray "optics". An x-ray optic, for example, as disclosed in U.S. Pat. No. 5,192,869 (the disclosure of which is included by reference herein in its entirety), is a device which diffracts x-rays so that the x-rays can be directed to a surface or object being treated or under examination, that is, to a target. However, in order to effectively direct x-rays to a target, the optic must be aligned with the source of x-rays so that the intensity of the x-rays arriving at the target is as great as possible. The present invention provides a method and apparatus for aligning an x-ray optic with an x-ray source to provide improved x-ray density on a target.

SUMMARY OF THE INVENTION

One aspect of the invention is a device for facilitating aligning an x-ray optic with a source of x-rays, the device including: a housing having a first aperture adapted to receive the x-ray optic; a surface positioned within the housing from which fluorescence occurs when x-rays directed by the x-ray optic impinge upon the surface; and wherein the housing with the x-ray optic is positionable relative to the source of x-rays, and wherein alignment is facilitated by monitoring fluorescence from the surface while moving the housing relative to the source of x-rays. In one aspect of the invention, the housing may further include a second aperture through which fluorescence from the surface can be monitored, for example, the second aperture may include an x-ray impermeable window. In another aspect of the invention, the device may further include means for moving the surface relative to the x-ray optic, for example, a threaded rod threaded to the housing and operatively connected to the surface. In another aspect of the invention, the device may further include means for monitoring fluorescence from the surface, for example, a camera or a CCD device. The device may be used for any type of x-ray optic, including a monocapillary optic, a polycapillary optic, a crystal optic, replicated optic, and a multilayer crystal optic, among others.

Another aspect of the invention is a device for facilitating determining a focusing characteristic of an x-ray optic, the optic being provided with a source of x-rays, the device including: a housing having a first aperture adapted to receive the x-ray optic; a surface positioned within the housing from which fluorescence occurs when x-rays directed by the x-ray optic impinge upon the surface; and means for moving at least one of the x-ray optic and the surface, wherein fluorescence from the surface can be varied to facilitate determining the focusing characteristic of the x-ray optic. In one aspect of the invention, the focusing characteristic of the x-ray optic may be the focal length of the x-ray optic and wherein the means for moving at least one of the x-ray optic and the surface includes means for minimizing the size of fluorescence from the surface. In another aspect of the invention, the focusing characteristic of the x-ray optic may be the shape of the focused x-ray beam and wherein the means for moving at least one of the x-ray optic and the surface comprises means for varying size of fluorescence from the surface. In another aspect of the invention, the means for moving at least one of the x-ray optic and the surface may include means for moving the surface, for example, a threaded rod threaded to the housing and operatively connected to the surface. In another aspect of the invention, the housing includes a second aperture through which fluorescence from the surface can be detected, for example, an aperture having an x-ray impermeable window. In one aspect of the invention, the device may also further include means for monitoring fluorescence from the surface, for example, a camera and a CCD device. Again, as above, this device may be used for any type of x-ray optic, including a monocapillary optic, a polycapillary optic, a crystal optic, replicated optic, and a multilayer crystal optic, among others.

A further aspect of the invention is a method for facilitating aligning an x-ray optic with a source of x-rays using a device comprising a housing having a first aperture and a surface positioned within the housing from which fluorescence occurs when x-rays impinge upon the surface, the method including: disposing the x-ray optic in the first aperture with the output of the x-ray optic directed toward the surface; and moving the housing with the x-ray optic relative to the source of x-rays while monitoring fluorescence from the surface to facilitate aligning the x-ray optic with the source of x-rays. In one aspect of the invention, the housing may include a second aperture, and monitoring fluorescence may include monitoring fluorescence from the surface through the second aperture, for example, visually monitoring or automatedly monitoring fluorescence from the surface. In one aspect of the invention, the method may further include moving the surface relative to the optic to vary fluorescence from the surface. The method may be used for any type of x-ray optic, including a monocapillary optic, a polycapillary optic, a crystal optic, replicated optic, and a multilayer crystal optic, among others.

A still further aspect of the invention is a method for facilitating determining a focusing characteristic of an x-ray optic, the optic being provided with a source of rays, using a device comprising a housing having a first aperture and a surface positioned within the housing from which fluorescence occurs when x-rays impinge upon the surface, the method including: disposing the x-ray optic in the first aperture with the output of the x-ray optic directed toward the surface; and moving at least one of the x-ray optic and the surface wherein fluorescence from the surface can be varied to facilitate determining the focusing characteristic of the x-ray optic. In one aspect of the invention, the focusing characteristic may be the focal length of the x-ray optic and wherein moving at least one of the x-ray optic and the surface minimizes the size of fluorescence to facilitate determining the focal length of the x-ray optic. In another aspect of the invention, the focusing characteristic may be the shape of an x-ray beam produced by the x-ray optic and wherein moving at least one of the x-ray optic and the surface varies the size of fluorescence to facilitate determining the shape of the x-ray beam produced by the x-ray optic. In another aspect of the invention, the surface is moveable and wherein said moving at least one of the x-ray optic and the surface comprises moving the surface relative to the x-ray optic, the moveable surface may be mounted on a rod threaded into the housing and wherein moving the surface comprises rotating the threaded rod. In another aspect of the invention, the method may include monitoring fluorescence from the surface, for example, visually monitoring or automatedly monitoring fluorescence from the surface through the second aperture. Again, the method may be used for any type of x-ray optic, including a monocapillary optic, a polycapillary optic, a crystal optic, replicated optic, and a multilayer crystal optic, among others.

The present invention addresses many of the limitations of the prior art while providing advantages over the prior art which will become more apparent upon review of the attached drawings, description below, and attached claims.

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may best be understood by reference to the following detailed descriptions of the preferred embodiments and the accompanying drawings in which:

BEST MODE FOR CARRYING OUT THE INVENTION

Figure 1:
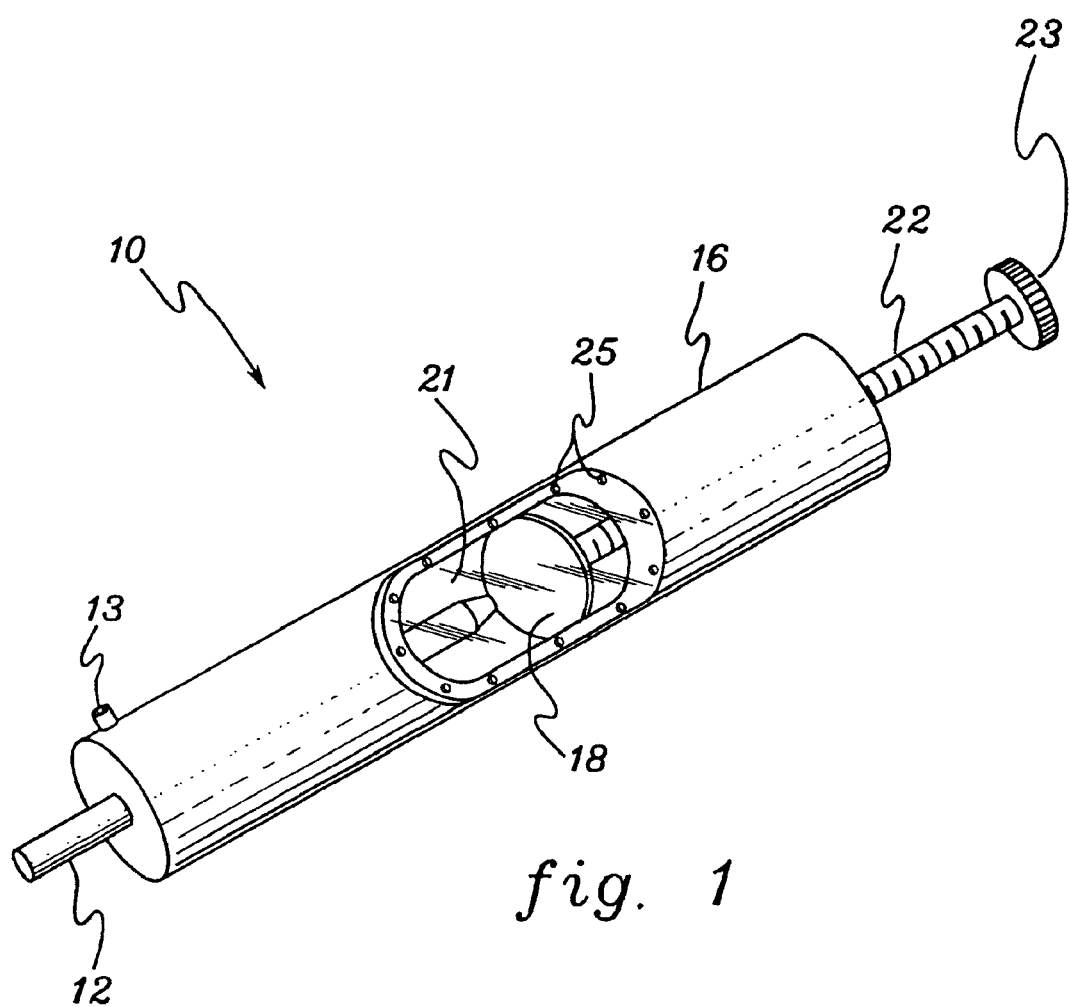
FIG. 1 is a perspective view of an x-ray alignment and imaging device according to one aspect of the present invention.
Figure 2:
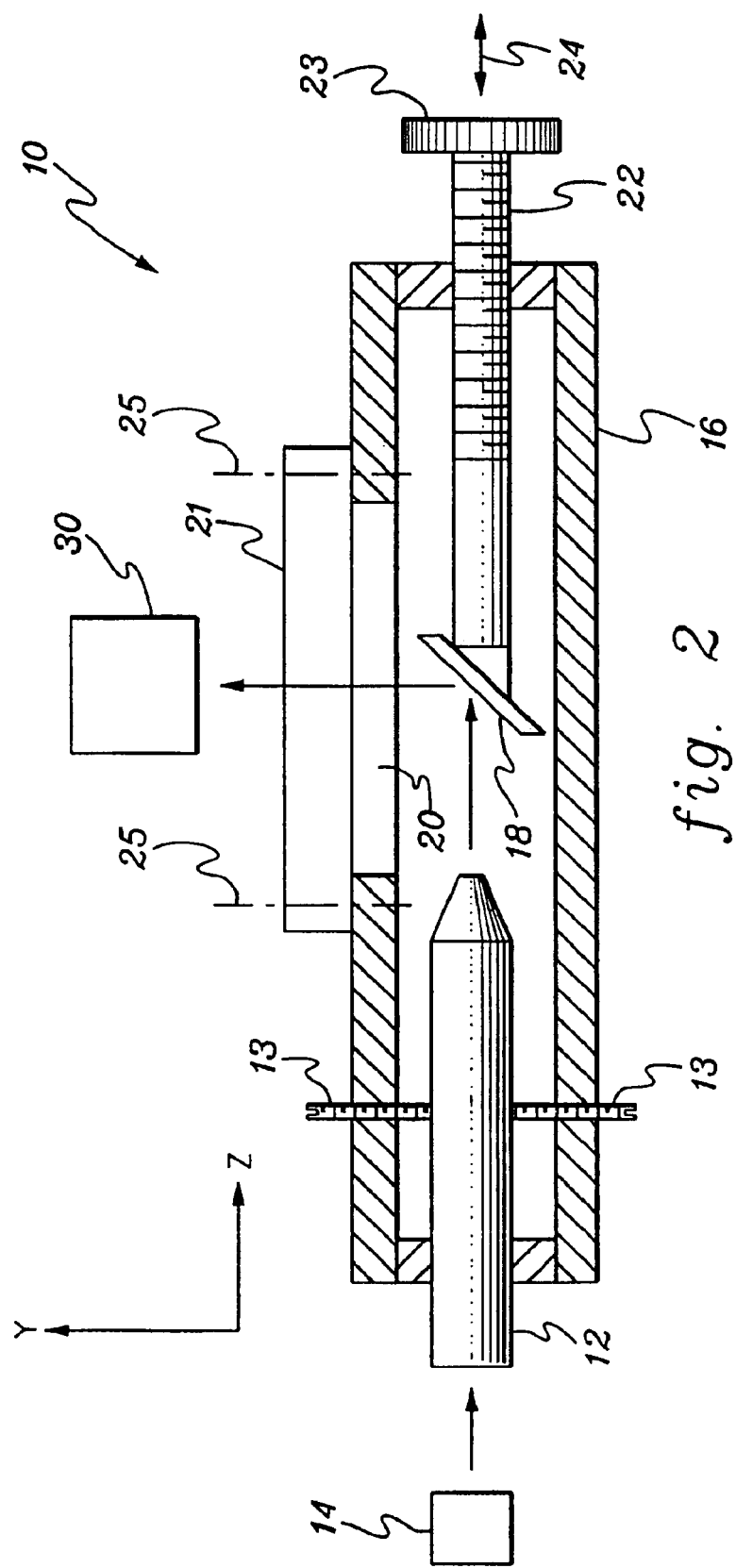
FIG. 2 is a cross-sectional, elevation view of the x-ray alignment and imaging device shown in FIG. 1, in accordance with one aspect of the present invention.

FIG. 1 illustrates a perspective view of a device 10 according to one aspect of the present invention. FIG. 2 illustrates a cross-sectional view of device 10 shown in FIG. 1. Device 10 allows a user to visually align an optic, for example, a polycapillary optic, 12 to an x-ray source 14 (see FIG. 2). The types of optics that can be aligned are not limited to polycapillary, but may also include multi-layer crystals, single-curved crystals, doubly-curved crystals, and replicated optics, among others. Optic 12 may be a focusing, diverging, or collimating optic. X-ray source 14 may be any type of conventional x-ray source, for example, a rotating or stationary filament-based electron-bombardment x-ray generation source, though other types of x-ray sources may be used. In one aspect to the invention, optic 12 is rigidly mounted to a mounting plate associated with the x-ray source 14.

Device 10 includes a cylindrical housing 16 and a surface 18 on to which at least some of the x-rays from source 14 are directed by optic 12. Though a cylindrical housing is shown in FIGS. 1 and 2, the present invention is not limited to cylindrical housings, but the housing may take any desired shape, including square, round, or rectangular. Optic 12 may be retained in housing 16 by one or more set screws 13, though other types of retaining methods may be used. According to the present invention, surface 18 includes at least some flourescent material, for example, a photo-luminescent material which fluoresces when exposed to x-rays. One photo-luminescent material that may be used for this invention is phosphorus. As shown in FIG. 2, surface 18 is typically an inclined surface, for example, inclined at between about 30 degrees and about 60 degrees, typically about 45 degrees, to the axis of the optic 12. Housing 16 includes at least one aperture 20 which may include a window 21 for viewing surface 18. Window 21 may be mounted by a plurality of fasteners 25 or by other conventional means. Surface 18 is typically inclined so that the image produced on surface 18 can be readily viewed though window 21, for example, viewed by an operator or by a fluorescence detection device 30. Device 30 may be a video camera or CCD device for detecting the flourescent image produced on surface 18.

In one aspect of the invention, window 20 typically includes a transparent window 21. Though in one aspect of the invention, window 21 is transparent to visual light, window 21 may typically be impermeable to other types of radiation emitted by the flourescent material on surface 18, for example, impermeable to x-rays. In one aspect of the invention, device 10 provides direct visual feedback of the alignment of optic 12 to x-ray source 14. In another aspect of the invention, the axial position of surface 18 may be varied by means of threaded rod 22 having handle 23, which is operatively connected to surface 18 and is threaded to housing 16.

According to one aspect of the invention, when used with some optics (for example, a polycapillary optic), device 10 creates a self-contained, shielded x-ray environment when attached to an x-ray source, for example, source 14, and there is little or no radiation leakage. For example, the device is constructed to minimize the emission of x-rays from the device.

According to one aspect of the invention, optic 12 is typically aligned with x-ray source 14 in the x and y axes (that is, perpendicular to the axis of the x-rays) and in the z-axis (that is, the axis along the path of the x-rays, see the y-z axis shown in FIG. 2.). The x, y and z alignment allows the input focal spot of optic 12 to be positioned as close as possible to, if not directly upon, the focal spot located on the anode of x-ray source 14. At this location the transmission of x-rays through optic 12 is maximized.

The alignment device 10 and optic 12 can be directly coupled to source 14, for example, mounted to source 14 by appropriate mounting means, for example, bolted, or device 10 and optic 12 can be independently mounted away from source 14, such as on an optical table. One advantage of having device 10 directly coupled or mounted on source 14 is that the entire system can be shielded as a self-contained unit, not allowing any x-ray radiation to exit the system during alignment.

The axial location of surface 18 relative to housing 16 (as indicated by double arrow 24 in FIG. 2, may be varied by any conventional means, for example, by using motors, linear actuators, or, as shown in FIGS. 1 and 2, by manually operating a shaft or rod, for example, a threaded rod, for instance, a fine-pitched adjustment screw. Other means, for example, pneumatical means, hydraulic means, and electromechanical means, among other means of moving surface 18, may also be used.

According to one aspect of the present invention, the x-ray image on surface 18 may by provided by using a material that emits radiation, for example, visible light, when excited by x-rays, for example phosphorous, though other radiation-emitting materials emitting any detectable form of electromagnetic radiation that may be detected visually or by a suitable detector may be used.

Window 21 may be made of any material that is transparent to the type of radiation emitted from surface 18. In the aspect of the invention shown in FIGS. 1 and 2, window 21 is transparent to visible light (that is, it's "clear"), while being opaque to x-rays. In one aspect of the invention, when the light-emitting material fluoresces when x-rays strike surface 18, the visible light emitted by the material on surface 18 can be viewed through window 21, while the viewer is protected from x-rays. Thus, window 20 provides a visual image of the x-rays being diffracted by optic 12 on to surface 18.

According to one aspect of the invention, the user positions device 10 relative to optic 12 so that an image appears on the flourescent material on surface 18, that is, positioned in x, y, and z directions. In one aspect of the invention device 10 may be moved relative to optic 12. In another aspect of the invention optic 12 is moved relative to device 10. This positioning of optic 12 relative to device 10 may be practiced manually or it may be automated. The relative positioning of optic 12 and device 10 may require the positioning of optic 12 relative to source 14. The positioning of optic 12 relative to source 14 may be aided by one or more positioning devices, for example, a device for positioning optic 12 in the x and y plane. This positioning of optic 12 so that an image appears on surface 18 aligns the input focal spot of optic 12 relative to x-ray source 14. During this alignment, typically in the z direction, as the focal spot of optic 12 approaches the source spot of source 14, the intensity and/or size of the fluorescence, for example, the size of the visual image, upon the fluorescent material on surface 18 varies. The alignment of optic 12 can thus be changed until the image, for example, the visual image, on surface 18 as viewed through window 20 is optimized, for example, provides for maximum intensity. Once optic 12 is positioned and aligned in the z direction as desired, optic 12 can be retained, for example, by set screws 13.

Once the position of optic 12 is established so that an image appears on surface 18, fine adjustment of the image can be obtained by moving surface 18 relative to housing 16. For example, surface 16 may be moved by means of a shaft or rod, for example a threaded rod, 22, either manually by using handle 23 or by automated means, for example, by means of a stepper motor. This fine adjustment of the location of surface 18 can be used to vary the size and shape of the image on surface 18 or to locate the focal length of optic 12. For example, for an optic 12 that is a focusing optic, as the position of surface 18 approaches the focal length of the optic, the size of the flourescent image on surface 18 will decrease. (When a collimating optic is used, the image will typically not decrease to a point, but remain essentially the shape of the optic, typically a circular or elliptical shape. When the optic is a diverging optic, the shape of the image will typically increase.) The size of the image will be minimum (theoretically a point) when the surface 18 is located at the focal length of optic 12. This focal length can then be measured, recorded for future reference, or, for example, compared to the theoretical focal length of the optic. Device 10 may also be calibrated, for example, device 10 may have a graduated scale, for example, on window 21 or rod 22, to indicate the relative position of surface 18 as surface 18 is moved within device 10. The movement of surface 18 relative to housing 16 also allows the operator to examine the variation of the shape of the image provided by optic 12 as the location of surface 18 varies, for example, relative to the focal length.

According to this aspect of the invention, the user of the alignment device is shielded from exposure to x-rays while visually allowing the user to see the direct output of the x-ray beam from the optic 12 on surface 18. This feature is accomplished by using a clear window that prevents the transmission of x-rays through it (such as acrylic impregnated with lead). Through this window, the user can view the image on the surface 18.

In one aspect of the invention, the image on surface 18 is simply viewed through window 21. However, according to another aspect of the invention, the image on surface 18 can detected by detection device 30, for example, a video camera or CCD camera and viewed on a video screen. The detected image may also be captured, manipulated or processed, and then displayed using software. In one aspect of the invention, the camera or detector 30 can be mounted directly to aperture 20 in housing 16. In addition, a means of magnifying the image may be included, for example, via software or simply by means of a conventional magnifying lens.

One embodiment of the device according to one aspect of the present invention was fabricated and was used to align a polycapillary-type focusing optic 12 to a filament-based electron-bombardment x-ray generation source 14. The polycapillary optic 12 was aligned by means of a manual x-y-z alignment device directly attached to source 14. As optic 12 was aligned to the anode of source 14, the variation in the image brightness was observed on the imaging surface 18. The alignment device 10 fabricated according to the present invention was attached directly to the polycapillary optic 12 by set screws 13. Visual feedback for the image produced on surface 18 was obtained by using a phosphorous material attached to a lead-impregnated disk mounted at a 45-degree angle. The disk was mounted on a threaded axial adjustment rod 22 whereby the axial or z-position of the disk could be varied. The light emitting material emitted visible light when x-rays from optic 12 struck the material on surface 18. The 45-degree angle of surface 18 allowed the light to be projected at an orthogonal angle from the plane of the x-ray beam provided by optic 12. A lead/acrylic window 21 was used to allow for viewing the emitted light. By using the 45 degree imaging plane, a convenient means of adjusting the output image on surface 18 relative to the output focal spot in the z-plane was obtained. The operator could easily view the image in the plane of the x-ray beam. In the actual set-up according to the present invention, the operator was able to view the alignment of the beam directly in the plane of the x-ray beam as opposed to viewing the orthogonal position of the beam.

The device fabricated according to the present invention was designed to allow attachment of a magnifying glass or a CCD camera. The magnifying glass allows the operator to visually align a focusing optic having a relatively small focal spot, that would otherwise be difficult to align due to the small image that is produced on surface 18. The CCD camera allows the user to examine the alignment of the optic using video capturing software.

In one aspect of the invention an inert gas may be provided to housing 16 or housing 16 may be operated under vacuum. These aspects of the invention, allow for the detection of low energy x-rays that may otherwise be absorbed or deflected by gas molecules in the housing. Nitrogen, helium, or another inert gasses may be used. The inert gas may be provided as a continuous purge or as a stationary gas. It will be apparent to those of skill the art that appropriate seals and gas/vacuum ports can be used to supply and evacuate gases from housing 16.

Thus, the present invention provides a method and apparatus for aligning x-the rays generated by an x-ray source and focused by an x-ray optic. Aspects of the present invention may have one or more of the following advantages compared to the prior art. The present invention permits users to safely align optics to sources without the use of large shielded enclosures. The present invention permits users to quickly align and test optics without the need for expensive detectors or computer software. The present invention permits realtime and visible alignment feedback to the user of a source optic system. The present invention facilitates the alignment of portable x-ray focusing systems and the alignment of sensors that use x-ray beams. In addition, the present invention provides for quick field service or laboratory based calibration of x-ray systems, x-ray beams and x-ray sensors and also allows users to visibly demonstrate optics to, for example, customers.

While the invention has been particularly shown and described with reference to one aspect of one embodiment, it will be understood by those skilled in the art that various changes in form and detail may be made to the invention without departing from the spirit and scope of the invention described in the following claims.

What is claimed is:

1. A device for facilitating aligning an x-ray optic with a source of x-rays, the device comprising:
    a housing having a first aperture adapted to receive the x-ray optic;
    a surface positioned within the housing from which fluorescence occurs when x-rays directed by the x-ray optic impinge upon the surface; and
    wherein the housing with the x-ray optic is positionable relative to the source of x-rays, and wherein alignment is facilitated by monitoring fluorescence from the surface while moving the housing relative to the source of x-rays.

2. The device as recited in claim 1, wherein the housing further comprises a second aperture through which fluorescence from the surface can be monitored.

3. The device as recited in claim 2, wherein the second aperture comprises an x-ray impermeable window.

4. The device as recited in claim 1, further comprising means for moving the surface relative to the x-ray optic.

5. The device as recited in claim 4, wherein the means for moving the surface comprises a threaded rod threaded to the housing and operatively connected to the surface.

6. The device as recited in claim 1, wherein the housing is a cylindrical housing.

7. The device as recited in claim 1, further comprising means for monitoring fluorescence from the surface.

8. The device as recited in claim 7, wherein the means for monitoring fluorescence from the surface comprises one of a camera and a CCD device.

9. The device as recited in claim 1, further comprising means for magnifying fluorescence from the surface.

10. The device as recited in claim 1, wherein the x-ray optic comprises one of a monocapillary optic, a polycapillary optic, a crystal optic, replicated optic, and a multilayer crystal optic.

11. The device as recited in claim 1, wherein the device is constructed to minimize emission of x-rays from the device.

12. The device as recited in claim 1, wherein the housing contains one of an inert gas and a vacuum.

13. A device for facilitating determining a focusing characteristic of an x-ray optic, the optic being provided with a source of x-rays, the device comprising:
    a housing having a first aperture adapted to receive the x-ray optic;
    a surface positioned within the housing from which fluorescence occurs when x-rays directed by the x-ray optic impinge upon the surface; and
    means for moving at least one of the x-ray optic and the surface, wherein fluorescence from the surface can be varied to facilitate determining the focusing characteristic of the x-ray optic.

14. The device as recited in claim 13, wherein the focusing characteristic of the x-ray optic comprises a focal length of the x-ray optic and wherein the means for moving at least one of the x-ray optic and the surface comprises means for minimizing size of fluorescence from the surface.

15. The device as recited in claim 13, wherein the focusing characteristic of the x-ray optic comprises a shape of the focused x-ray beam and wherein the means for moving at least one of the x-ray optic and the surface comprises means for varying size of fluorescence from the surface.

16. The device as recited in claim 13, wherein the means for moving at least one of the x-ray optic and the surface comprises means for moving the surface.

17. The device as recited in claim 16, wherein the means for moving the surface comprises a threaded rod threaded to the housing and operatively connected to the surface.

18. The device as recited in claim 13, wherein the housing comprises a second aperture through which fluorescence from the surface can be detected.

19. The device as recited in claim 18, wherein the second aperture comprises an x-ray impermeable window.

20. The device as recited in claim 13, wherein the housing comprises a cylindrical housing.

21. The device as recited in claim 13, further comprising means for monitoring fluorescence from the surface.

22. The device as recited in claim 21, wherein the means for monitoring fluorescence comprises one of a camera and a CCD device.

23. The device as recited in claim 13, further comprising means for magnifying fluorescence from the surface.

24. The device as recited in claim 13, further comprising a graduated scale for determining location of the surface relative to the x-ray optic.

25. The device as recited in claim 13, wherein the x-ray optic comprises one of a monocapillary optic, a polycapillary optic, a crystal optic, replicated optic, and a multilayer crystal optic.

26. The device as recited in claim 13, wherein the device is constructed to minimize emission of x-rays from the device.

27. The device as recited in claim 13, wherein the housing contains one of an inert gas and a vacuum.

28. A method for facilitating aligning an x-ray optic with a source of x-rays using a device comprising a housing having a first aperture and a surface positioned within the housing from which fluorescence occurs when x-rays impinge upon the surface, the method comprising:
    disposing the x-ray optic in the first aperture with the output of the x-ray optic directed toward the surface; and moving the housing with the x-ray optic relative to the source of x-rays while monitoring fluorescence from the surface to facilitate aligning the x-ray optic with the source of x-rays.

29. The method as recited in claim 28, wherein the housing comprises a second aperture, and monitoring fluorescence comprises monitoring fluorescence from the surface through the second aperture.

30. The method as recited in claim 28, wherein monitoring the fluorescence comprises one of visually monitoring and automatedly monitoring fluorescence from the surface.

31. The method as recited in claim 28, further comprising moving the surface relative to the optic to vary fluorescence from the surface.

32. The method as recited in claim 28, wherein the x-ray optic comprises one of a monocapillary optic, a polycapillary optic, a crystal optic, replicated optic, and a multilayer crystal optic.

33. The method as recited in claim 28, wherein the method is practiced wherein emission of x-rays from the device is minimized.

34. The method as recited in claim 28, wherein the method further comprises providing one of an inert gas and vacuum to the housing.

35. A method for facilitating determining a focusing characteristic of an x-ray optic, the optic being provided with a source of rays, using a device comprising a housing having a first aperture and a surface positioned within the housing from which fluorescence occurs when x-rays impinge upon the surface, the method comprising:
  disposing the x-ray optic in the first aperture with the output of the x-ray optic directed toward the surface; and
  moving at least one of the x-ray optic and the surface wherein fluorescence from the surface can be varied to facilitate determining the focusing characteristic of the x-ray optic.

36. The method as recited in claim 35, wherein the focusing characteristic comprises a focal length of the x-ray optic and wherein moving at least one of the x-ray optic and the surface minimizes size of fluorescence to facilitate determining the focal length of the x-ray optic.

37. The method as recited in claim 35, wherein the focusing characteristic comprises a shape of an x-ray beam produced by the x-ray optic and wherein moving at least one of the x-ray optic and the surface varies the size of fluorescence to facilitate determining the shape of the x-ray beam produced by the x-ray optic.

38. The method as recited in claim 35, wherein the surface is moveable and wherein said moving at least one of the x-ray optic and the surface comprises moving the surface relative to the x-ray optic.

39. The method as recited in claim 38, wherein the moveable surface is mounted on a rod threaded into the housing and wherein moving the surface comprises rotating the threaded rod.

40. The method as recited in claim 35, further comprising monitoring fluorescence from the surface.

41. The method as recited in claim 40, wherein the housing comprises a second aperture, and wherein monitoring fluorescence comprises monitoring fluorescence through the second aperture.

42. The method as recited in claim 40, wherein monitoring fluorescence comprises one of visually monitoring and automatedly monitoring fluorescence.

43. The method as recited in claim 35, wherein the x-ray optic comprises one of a monocapillary optic, a polycapillary optic, a crystal optic, replicated optic, and a multilayer crystal optic.

44. The method as recited in claim 35, wherein the method is practiced wherein emission of x-rays from the device is minimized.

45. The method as recited in claim 35, wherein the method further comprises providing one of an inert gas and vacuum to the housing.

* * * * *